United States Patent [19]

Behling et al.

[11] Patent Number: 5,286,877
[45] Date of Patent: Feb. 15, 1994

[54] SYNTHESIS OF 1,4-DIDEOXY-1,4-IMINO-L-ARABINITOL

[75] Inventors: James R. Behling, Lindenhurst; John R. Medich, Des Plaines; Kevin A. Babiak, Evanston, all of Ill.; George W. J. Fleet, Oxford, United Kingdom

[73] Assignee: G. D. Searle & Co., Skokie, Ill.

[21] Appl. No.: 12,077

[22] Filed: Feb. 1, 1993

[51] Int. Cl.$^5$ ............... C07D 207/12; C07D 207/24; C07D 207/36
[52] U.S. Cl. .................................................. 548/556
[58] Field of Search ........................................ 548/556

[56] References Cited

U.S. PATENT DOCUMENTS 4,876,268  10/1989  Koszyk et al. ............. 514/425
4,910,310   3/1990  Campbell et al. ........... 546/116
5,089,520   2/1992  Fleet et al. ................ 514/425

OTHER PUBLICATIONS

Wang et al., Tetrahedron: Asymmetry, vol. 1, No. 8, pp. 527–530 (1990).
Fleet et al., J. Chem. Soc., Perkin Trans. 1, pp. 665–666 (1989).

*Primary Examiner*—Johann Richter
*Attorney, Agent, or Firm*—Scott J. Meyer

[57] ABSTRACT

1,4-Dideoxy-1,4-imino-L-arabinitol is chemically synthesized from D-lyxonolactone by formation of the pyrrolidine ring by joining the nitrogen between C-1 and C-4 and inversion of configuration at both C-2 and C-4, with the C-3 and C-5 hydroxyl groups being protected throughout the synthesis sequence by benzylidenation. The product is preferably isolated as the hydrochloride salt and is useful as an inhibitor of $\alpha$-glucosidase and human immunodeficiency virus (HIV).

5 Claims, No Drawings

SYNTHESIS OF 1,4-DIDEOXY-1,4-IMINO-L-ARABINITOL

BACKGROUND OF THE INVENTION

This invention relates to a method for the chemical synthesis of 1,4-dideoxy-1,4-imino-L-arabinitol.

Both the D and L enantiomers of 1,4-dideoxy-1,4-imino-arabinitol are known compounds. They can be described alternatively as analogues of furanose sugars or as polyhydroxylated pyrrolidines.

Analogues of sugars, in which the ring oxygen has been replaced by nitrogen and the anomeric oxygen has been removed, usually[1] but not always[2] cause inhibition of the enzymic hydrolysis of the corresponding glycosidic bond. Although a number of naturally occurring analogues of hexoses containing six or more carbon atoms have been reported[3], nitrogen analogues of only two pentoses, 2-deoxyribose and D-arabinose, have so far been isolated as natural products and these are pyrrolidine rather than piperidine derivatives. CYB3 (1), an analogue of 2-deoxyribose, was isolated from *Castanospermum australe*[4] although, as yet, no significant biological activity has been described. Nectrisine (2),[5] an imine nominally derived from dehydration of 4-amino-4-deoxy-D-arabinose, is an immunomodulator isolated from a fungus which shows potent inhibition of α-glucosidase and α-mannosidase activity.[6] DAB1 [1,4-Dideoxy-1,4-imino-D-arabinitol] (3), isolated from both *Angylocalyx boutiqueanus*[7] and *Arachniodes standishii*,[8] is a powerful inhibitor of yeast α-glucosidase[9] and also inhibits different mouse gut dissacharidases to different degrees.[10] Some studies on the mechanism of insect antifeedant activity of DAB1 have been reported;[11] additionally, compounds such as DAB1 may be carcinogenic to rodents.[12] Also DAB1 inhibits the hydrolysis of sinigrin and progoitrin by thioglucosidases from mustard and the cabbage aphid, *Brevicoryne brassicae*.[13] DAB1 also inhibits phloem unloading and/or utilization of sucrose, resulting in insufficient sucrose transport from cotyledons to roots and hypocotyls.[14]

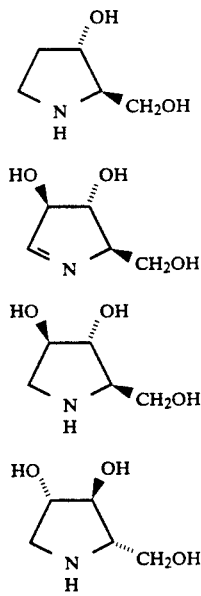

The structure of DAB1 (3) was established by synthesis of both DAB1 and its enantiomer LAB1 (4) from L-arabinose[15] and from D-xylose.[9,16] Other syntheses of DAB1 and its stereoisomers have been reported from carbohydrate[17] and other chiral pool starting materials,[18] by sequences involving the use of aldolases as the key step,[19] and by other methods.[20] LAB1 (4) was shown to be a potent inhibitor of the α-L-arabinofuranosidase III of *Monilinia fructigena*;[21] although LAB1 is a much weaker inhibitor of yeast α-glucosidase than is the natural product DAB1, LAB1 is a much more powerful inhibitor of some mouse gut α-glucosidases than is DAB1;[22] molecular modifying studies have been used to account for the observation that LAB1 is about ten times more powerful an inhibitor of sucrase than DAB1[23]. A number of polyhydroxylated nitrogen heterocycles were screened as agents for the inhibition of HIV-induced syncthia formation,[24] of which LAB1 was among the most powerful antiviral agents.[25] Derivatives of LAB1 have also been shown to have antiviral activity.[26]

The use of LAB1 as a strong inhibitor of human immunodeficiency virus (HIV) is further disclosed in U.S. Pat. No. 5,089,520, and its use as an intermediate in the synthesis of antiviral derivatives is disclosed in U. S. Pat. No. 4,876,268.

BRIEF DESCRIPTION OF THE INVENTION

In accordance with the present invention, a novel method for the synthesis of 1,4-dideoxy-1,4-imino-L-arabinitol (LAB1) is provided. The method comprises a multi-step synthesis from the known compound, D-lyxonolactone (5).

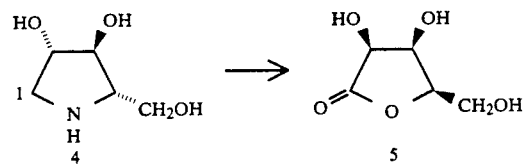

Although D-lyxonolactone (5) is readily available from oxygenation of an alkaline solution of D-galactose,[27] there are very few examples of its use as a constituent of the chiral pool. It has been used for efficient syntheses of the fucosidase inhibitor deoxyfuconojirimycin[28] and of the potent antiviral oxetane nucleoside epinoroxetanocin.[29]

The synthesis of LAB1 (4) from D-lyxonolactone (5) in accordance with the present invention comprises the formation of the pyrrolidine ring by the joining by nitrogen between C-1 and C-4 and inversion of configuration at both C-2 and C-4, with the C-3 and C-5 hydroxyl groups being protected throughout the sequence by benzylidenation.

Synthesis of LAB1 from D-lyxonolactone is preferably carried out by the following stepwise method in which compound numbers in parentheses correspond to compounds shown by chemical structure herein. This preferred method comprises:

a) introducing a protecting group at C-3 and C-5 by reacting D-lyxonolactone (5) with benzaldehyde to give the benzylidine derivative (6), b) esterifying the benzylidine derivative (6) at C-2 with mesyl chloride to give the corresponding mesylate (7), c) reducing the mesylate (7) with lithium borohydride to open up the ring and give the corresponding D-lyxitol (8), d) reacting the D-lyxitol (8) with potassium carbonate in alcoholic solution to give the corresponding C-1/C-2 epoxide (9),
e) esterifying the epoxide (9) with triflic anhydride to give the corresponding triflate ester (10),
f) introducing the azide group at C-4 in the triflate ester (10) to give the corresponding azidoepoxide (11),
g) reducing the azide group of azidoepoxide (11) by catalytic hydrogenation to provide the corresponding amine (12),
h) reacting amine (12) with tetrabutylammonium iodide to provide ring closure to the desired pyrrolidine structure and give the corresponding protected 1,4-imino-L-arabinitol (13),
i) removing the benzylidine protecting group of the protected 1,4-dideoxy-1,4-imino-L-arabinitol (13) by acid hydrolysis to give the desired 1,4-dideoxy-1,4-imino-L-arabinitol.

Other such suitable reactants for use in the foregoing synthesis of 1,4-dideoxy-1,4-imino-L-arabinitol will be readily apparent to the person skilled in the art after reading the present disclosure. These reactants are generally used in proportions such as to satisfy the stoichiometry of the aforesaid reaction steps. Illustrative of suitable reactants are the use of a noble metal catalyst such as palladium and platinum in the catalytic hydrogenation step; use of alkali metal azides such as sodium, lithium and potassium azides for introducing the azide group; use of alcohols such as methanol, ethanol and isopropanol as a solvent medium for the reaction of the mesylate with potassium carbonate to produce the epoxide; use of aqueous acids such as trifluoroacetic acid, hydrochloric acid and sulfuric acid for hydrolytic removal of the protecting group; use of tetrabutylammonium iodide and similar such iodides for the ring closure step; and use of lithium borohydride and similar such hydrides for the reduction of the mesylate.

DETAILED DESCRIPTION OF THE INVENTION

The invention is conveniently illustrated by the following detailed description of the preferred embodiments in which 1,4-dideoxy-1,4-imino-L-arabinitol is synthesized from D-lyxonolactone by formation of the pyrrolidine ring by joining the nitrogen between C-1 and C-4 and inversion of configuration at both C-2 and C-4, with the C-3 and C-5 hydroxyl groups being protected throughout the synthesis sequence by benzylidenation.

According to these detailed illustrative embodiments, treatment of D-lyxonolactone (5) with benzaldehyde and aqueous concentrated hydrochloric acid gave the benzylidene derivative (6) [96%] in which only the C-2 hydroxyl group remains free; the configuration of the benzylidene carbon has been established by an X-ray crystal structure of a benzylidene derivative of epinoroxetanocin formed from (6).[29] Esterification of (6) with mesyl chloride in pyridine afforded the mesylate (7) [83%] which was reduced to the diol (8) by lithium borohydride in tetrahydrofuran [90%]. Reaction of (8) with potassium carbonate in methanol gave the epoxide (9) [80%]; there was no competition from formation of the alternative oxetane derived by attack from the C-4 hydroxyl. Treatment of (9) with triflic anhydride gave the corresponding triflate (10) which was further reacted with sodium azide to give the azidoepoxide (11) [92%]. Hydrogenation of the azide (11) in the presence of palladium gave the amine (12) [62%]. Closure of (12) to the required pyrrolidine (13) would require a forbidden 5-endo-tet process;[30] accordingly, (12) was treated with tetrabutylammonium iodide to give an intermediate iodoalcohol which spontaneously closed to afford (13) [76%]. Finally, the benzylidene protecting group in (13) was removed by aqueous acid to give LAB1 (4), which was most conveniently isolated as the hydrochloride [84%] although other pharmaceutically acceptable salts of the free sugar amine can also be prepared in the final step. The overall yield of LAB1 from D-lyxonolactone was 21% in these illustrative embodiments.

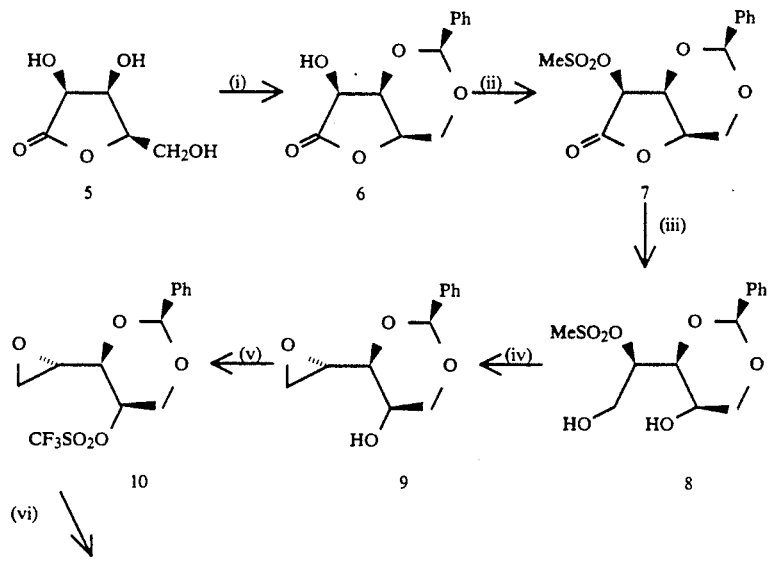

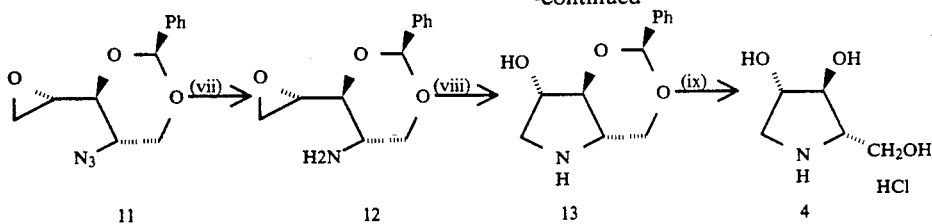

(i) PhCHO, conc. HCl (ii) MeSO₂Cl, pyridine (iii) LiBH₄, THF (iv) K₂CO₃, MeOH (v) (CF₃SO₂)₂, pyridine, CH₂Cl₂ (vi) NaN₃, DMF (vii) H₂, 5% Pd/C, MeOH (viii) Bu₄NI, THF (ix) aq. H₂SO₄; then aq. HCl The disclosed invention thus provides an efficient synthesis of the antiviral aminosugar LAB1 (4) and further demonstrates the value of D-lyxonolactone as a desirable starting material from the chiral pool.

The following specific examples will further illustrate the invention in greater detail although it will be appreciated that the invention is not limited to these specific examples or the details therein.

EXAMPLES

General Procedures

Proton nuclear magnetic resonance ($\delta_H$) spectra were recorded at 200 MHz or 400 MHz on Varian VXR200 or VXR400 spectrometers, respectively. All chemical shifts are quoted on the δ-scale. Infra-red spectra were recorded on Perkin Elmer 281 spectrophotometer. Optical rotations were measured on a Perkin Elmer 241 polarimeter with a path length of 1 dm. Concentrations were given in g/100 ml. Microanalyses were performed on a CEC240 automatic elemental analyzer. Thin layer chromatography (t.l.c.) was carried out on aluminum sheets coated with 60F₂₅₄ silica. Plates were developed using either 5% v/v concentrated sulphuric acid in methanol, 0.2% w/v cerium (IV) sulphate and 5% ammonium molybdate in 2M sulphuric acid and 0.5% ninhydrin in methanol. Flash chromatography was carried out using Merck 60 silica. Solvents and commercially available reagents were dried and purified before use according to standard procedures; dichloromethane was refluxed over and distilled from calcium hydride, N,N-dimethylformamide was distilled under reduced pressure from calcium hydride, methanol was distilled from magnesium methoxide, pyridine was distilled from, and stored over, potassium hydroxide and tetrahydrofuran was distilled from a purple solution of sodium benzophenone ketyl immediately before use. Hexane was distilled at 68° C. before use to remove involatile fractions. Lyxono-1,4-lactone (5) was prepared from D-galactose as previously described.[27]

EXAMPLE 1

3.5(S)-O-Benzylidene-D-lyxono-1,4-lactone (6)

D-Lyxono-1,4-lactone (5) (75 g, 0.507 mole) was dissolved in benzaldehyde (750 ml) and cooled to 0° C. using an ice bath. Concentrated hydrochloric acid (75 ml. 12N) was added over a one hour time period after which the reaction mixture was allowed to mix at this temperature for three hours. The reaction mixture was allowed to come to room temperature and was stirred at this temperature overnight (14 h). The reaction mixture was again cooled to 5° C. using an ice bath and was diluted with cold ether (1.6 l). The resulting mixture was stirred rapidly, and a saturated solution of sodium bicarbonate (500 ml) was added slowly. The resulting mixture was filtered and the filter cake was washed with cold ether to provide the crude product. The residue was recrystallized from ethanol (2 l) to provide 3.5(S)-O-benzylidene-(6) as a white solid (114 g, 96%), m.p. 203°–204° C.; $v_{max}$ (KBr): 3450, 1770, 1380, 1185; 1150, 1050, 1010, 700 cm⁻¹; ¹H NMR (DMSO d6) ∂ 4.15 (d, 1 H), 4.25 (d, 1 H), 4.40 (d, 2 H), 4.70 (m, 2 H), 5.65 (s, 1 H), 6.05 (d, 1 H), 7.40 (m, 5 H); ¹C NMR (DMSO d6) ∂ 6 65.80; 69.54, 70.86, 74.19, 97.60, 126.18, 127.89, 128.76, 137.70, 175.96; $[\alpha]_{D25}$ +40.1° (c 1.0, DMSO). (Found: C, 60.64; H, 5.12%. C₁₂H₁₂O₅ requires C,61.01; H, 5.12%).

EXAMPLE 2

3.5(S)-O-Benzylidene-2-O-methanesulphonyl-D-lyxono-1,4-lactone (7)

Methanesulfonyl chloride (62 g, 42 ml, 0.542 mole) was added dropwise to a solution of 3,5(S)-O-benzylidene-D-lyxono-1,4-lactone (6) (113 g, 0.478 mole) in pyridine (500 ml) over a twenty minute time period at ambient temperature. The resulting reaction mixture was stirred at ambient temperature for three additional hours. The reaction mixture was then diluted with cold water (2 l) to complete the precipitation of the product. The resulting solids were isolated by filtration and the filter cake was washed with cold water (2 l). After pulling the filter cake dry, the crude product was dissolved in hot acetone (1 l) and filtered through a plug of glass wool. The resulting solution was heated to reflux, and hot isopropanol (500 ml) was added with agitation. The solution was cooled to room temperature and then to 5° C. using an ice bath. The product (104.4 g) was isolated by filtration and the resulting white crystalline material was dried in a vacuum oven; a second crop (19.5 g) of equal purity was obtained from the filtrate to afford 3.5(S)-O-benzylidene-2-O-methanesulphonyl-D-lyxono-1,4-lactone (7), (123.9 g, 83%), m.p. 116.5°–117° C.; $v_{max}$(KBr): 3410, 2930, 1775, 1370, 1180, 1105, 1040, 1000, 965, 820, 700 cm⁻¹; ¹H NMR (DMSO d6) ∂ 3.32 (s, 1 H), 3.36 (s, 3 H), 4.32 (ABX, 2 H), 4.62 (d, 1 H), 5.10 (m, 1 H), 5.71 (s, 1 H), 5.91 (d, 1 H), 7.40 (s, 5 H); ¹³C NMR (DMSO d6) ∂ 38.67, 65.48, 70.42, 72.55, 75.76, 97.55, 125.95, 128.06, 128.96, 137.14, 170.39; $[\alpha]_{D25}$ +66.3° (c 0.95, DMSO) . (Found: C, 49.63; H, 4.51; S, 10.18%. C₁₃H₁₄O₇S requires C, 49.68; H, 4.49; S, 10.20%).

EXAMPLE 3

3,5(S)-O-Benzylidene-2-O-methanesulphonyl-D-lyxitol (8)

Lithium borohydride (198 ml, 2M in tetrahydrofuran, 0.396 mole) was added to a solution of 3,5(S)-O-benzylidene-2-O-methanesulphonyl-D-lyxono-1,4-lactone (7) (122 g, 0.388 mole) in tetrahydrofuran (1.5 l) at −68° C. over a fifteen minute time period under an atmosphere of argon. The resulting mixture was allowed to slowly warm to room temperature over a 25 min time period and then the reaction was stirred at ambient temperature for 16 hours. The reaction mixture was then cooled to 150° C. and quenched by the dropwise addition of saturated ammonium chloride solution (100 ml ). The resulting mixture was partitioned between ethyl acetate (500 ml) and water (100 ml ). The layers were separated and the aqueous layer was extracted with ethyl acetate (2×100 ml). The combined organic layers were dried over magnesium sulfate, filtered and concentrated to dryness by rotary evaporation to provide the crude product as a crystalline residue. The product was recrystallized from 2:3 acetone:hexane (500 ml) to provide 3,5(S)-O-benzylidene-2-O-methanesulphonyl-D-lyxitol (8), (111.23 g, 90%) as a white crystalline solid, m.p. 99°-100° C.; $\nu_{max}$ (KBr): 3490, 3390, 2910, 1410, 1350, 1340, 1170, 1090, 1020, 925, 770 cm$^{-1}$; $^1$H NMR (acetone d$_6$) $\partial$ 2.90 (bs, 1 H), 3.25 (s, 3 H), 3.65 (d, 1 H), 3.98 (ABX, 2 H), 4.22 (m, 3 H), 4.35 (t, 1 H), 4.85 (m, 1 H), 5.70 (s, 1 H), 7.38 (m, 3 H), 7.55 (m, 2 H); $^{13}$C NMR (acetone d$_6$) $\partial$ 38.46, 61.35, 63.10, 72.99, 77.25, 81.66, 101.91, 127.15, 128.77, 129.52, 139.44; $[\alpha]_{D25}$ −15.90° (c 1.03, acetone). (Found: C, 48.82; H, 5.85; S, 9.93%. $C_{13}H_{18}O_7S$ requires C, 49.05; H, 5.70; S, 10.07%).

EXAMPLE 4

1,2-Anhydro3,5(S)-O-benzylidene-D-xylitol (9)

Potassium carbonate (52.5 g, 0.380 mole) was added to a solution of 3,5(S)-O-benzylidene-2-O-methanesulphonyl-D-lyxitol (8) (110 g, 0.345 mole) in methanol (2 l). The resulting mixture was stirred for 24 hours at ambient temperature. The reaction mixture was concentrated to dryness by rotary evaporation leaving a white solid (170 g). This solid was digested with ether:acetone (1:1, 2 l) and the remaining solids were removed by filtration. The filtrate was concentrated to dryness by rotary evaporation leaving a off white solid (85 g). This solid was dissolved in hot acetone (300 ml) and then diluted with hot hexane (500 ml). After cooling to 50° C. the product was collected by filtration and rinsed with hexane. The product was dried in a vacuum oven leaving 1,2-anhydro-3,5(SX-O-benzylidene-D-xylitol (9), (61.3 g, 80%) as a white solid, m.p. 119°-120° C.; $\nu_{max}$ (KBr): 3470, 2910, 2860, 1400, 1290, 1140, 1090, 1020, 9901 960, 765 705 cm$^{-1}$; $^1$H NMR (CDCl$_3$) $\partial$ 2.75 (m, 1 H), 2.90 (t, 1 H), 2.99 (d, 1 H), 3.38 (m, 1 H) 3.65 (m, 2 H), 4.15 (ABq,, 2 H), 5.60 (s, 1 H), 7.40 (m, 3 H), 7.55 (m, 2 H). $^{13}$C NMR (CDCl$_3$) $\partial$ 43.47, 52.00, 65.14, 72.30, 81.37, 101.17, 125.92, 128.18, 129.05, 137.27; $[\alpha]_{D25}$+5.6° (c 0.952, CHCl$_3$). (Found: C, 64.45; H, 6.40%. $C_{12}H_{14}O_4$ requires C, 64.85; H, 6.35%).

EXAMPLE 5

1,2-Anhydro-4-azido-3,5(S)-O-benzylidene-4-deoxy-L-arabinitol (11)

Triflic anhydride (5.8 g; 3.5 ml, 20.6 mmol) was added dropwise to a −30° C. solution of 1,2-anhydro-3,5(S)-O-benzylidene-D-xylitol (9) (4.0 g, 18 mmol) and pyridine (2.8 g, 36.0 mmol) in dichloromethane (50 ml). The resulting mixture was stirred for 2 hours at ∼−30° C. The reaction mixture was then poured into water (60 ml) and the resulting mixture was stirred for 10 min. The layers were separated and the aqueous layer was extracted with two 25 ml portions of dichloromethane. The combined organic layers were washed once with brine (25 ml), dried over anhydrous sodium sulfate and filtered. The filtrate was concentrated to dryness by rotary evaporation leaving a yellow oil which was dried further under high vacuum for 2 hours affording the corresponding triflate (10) as a yellow solid (6.3 g, 100%); the triflate (10) was used in the next stage without further purification. Sodium azide (1.4 g, 21.6 mmol) was added portionwise to a 0° C. solution of the triflate (10) in dimethylformamide (20 ml). The resulting mixture was stirred for 2 hours at 0° C. The dimethylformamide was removed by rotary evaporation using high vacuum and the residue was dissolved in water (40 ml). The mixture was extracted with dichloromethane (4×25 ml) and the combined organic extracts were dried (sodium sulfate) and filtered. The filtrate was concentrated to dryness by rotary evaporation then under high vacuum to provide 1,2-anhydro-4-azido-3,5 (S)-O-benzylidene-4-deoxy-L-arabinitol (11), (4.1 g, 92%) as a yellow solid, m.p. 53°-54° C.; $\nu_{max}$ (KBr) : 4330; 30001 2880, 2120, 1450, 1380, 1285, 1150, 1080, 1030, 755, 705 cm$^{-1}$; $^1$H NMR (CDCl3) $\partial$ 2.95 (d, 2 H), 3.26 (m, 1 H), 3.50 (m, 1 H), 3.70 (m, 2 H), 4.40 (ABX, 2 H), 5.46 (s, 1 H), 7.38 (m, 3 H), 7.48 (m, 2 H); $^{13}$C NMR (CDCl$_3$) $\partial$ 44.11, 51.29, 54.40, 68.67, 80.05, 100.80; 126.00, 128.14, 129.07, 136.37; $[\alpha]_{D25}$+29.3° (c 1.02, CHCl$_3$). (Found: C, 58.17; H, 5.35; N, 17.01%. $C_{12}H_{13}O_3N_3$ requires C, 58.29; H, 5.30; N, 16.99%).

EXAMPLE 6

1 2 -Anhydro-4-amino-3,5(S)-O-benzylidene-4-deoxy-L-arabinitol (12)

A solution of 1,2-anhydro-4-azido-3,5(S)-O-benxylidene-4-deoxy-L-arabinitol (11) (4.0 g, 16.0 mmol) in the presence of 5% palladium on carbon (50% wet, 10.4 g) in methanol (75 ml) was placed under 5 psi hydrogen pressure for 30 min. The mixture was filtered and the filtrate was concentrated to dryness by rotary evaporation leaving the crude product (4 g) as a yellow solid. The product was purified by flash chromatography on a 60 mm column using 120 g of silica gel and 20/80 ethanol/CHCl$_3$ as the eluent. The appropriate fractions were combined and concentrated to dryness by rotary evaporation to provide 1,2-anhydro-4-amino-3,5(S)-O-benzylidene-4- deoxy-L-arabinitol (12), (2.2 g, 62%), m.p. 100°-102° C.; $\nu_{max}$ (KBr): 3300, 2970, 2860, 1600, 1450, 1390, 1100, 1030, 865, 750, 700 cm$^{-1}$; $^1$H NMR (CD$_3$OD) $\partial$ 2.90 (m, 2 H), 3.00 (m, 1 H), 3.22 (m, 1 H), 3.40 (dd, 1 H); 3.55 (t, 1 H), 4.20 (dd, 1 H), 4.60 (bs, 2 H), 5.50 (s, 1 H), 7.32 (m, 3 H), 7.45 (m, 2 H); $^{13}$C NMR (CD$_3$OD) $\partial$ 45.23, 47.09, 52.75, 72.69, 84.29, 101.87; 127.28, 128.94, 129.79, 139.34; $[\alpha]_{D25}$ +138.2° (c 0.997, CH$_3$OH). (Found: C, 64.99; H, 6.83; N, 6.15%. $C_{12}H_{15}O_3N$ requires C, 65.14; H, 6.83; N, 6.33%).

EXAMPLE 7

3,5(S)-O-Benzylidene-1,4-dideoxy-1,4-imino-L-arabinitol (13)

1,2-Anhydro-4-amino-3,5(S)-O-benzylidene-4-deoxy-L-arabinitol (12) (1.0 g, 4.5 mmol), tetrabutylammonium iodide (1.6 g; 4.5 mmol) and tetrahydrofuran (50 ml) were combined and heated at reflux for 72 hours. The cooled reaction mixture was filtered to remove the precipitated tetrabutylaramonium iodide and the filtrate was concentrated to dryness by rotary evaporation. The residue was dissolved in dichloromethane (60 ml) and concentrated to a volume of ∼25 ml using a steam bath. After cooling to 5° C. the product was collected by filtration and rinsed with ice-cold dichloromethane. The solid was dried under vacuum to provide the product (0.58 g, 58%) as a white solid. The filtrate was concentrated by rotary evaporation leaving a yellow oil (0.89 g) which was flash chromatographed to provide an additional 0.18 g of 3,5(S)-O-benzylidene-1,4-dideoxy-1,4-imino-L-arabinitol (13), (76% combined yield), m.p. 165.5°-166° C.; $v_{max}$ (KBr): 3400, 3300, 2860, 1620, 1450, 1375, 1150, 1045, 910, 690; $^1$H NMR (CD$_3$OD) ∂ 2.75 (dd, 1 H), 2.90 (m, 1 H), 3.40 (m, 1 H), 3.60 (m, 1 H), 3.84 (t, 1 H), 4.32 (m, 2 H), 4.85 (bs, 2 H), 5.55 (s 1 H), 7.35 (m, 3 H), 7.50 (m, 2 H); $^{13}$C NMR (CD$_3$OD) ∂ 51.19, 55.19, 72.81, 72.90, 88.34, 103.24, 127.44, 129.01, 129.86; 139.16; $[\alpha]_{D25}$+76.4° (c 0.725, CH$_3$OH). (Found: C,65.01; H, 6.86; N, 6.21%. C$_{12}$H$_{15}$O$_3$N requires C, 65.14; H, 6.83; N, 6.33%).

EXAMPLE 8

1,4-Dideoxy-1,4-imino-L-arabinitol hydrochloride [L-AB1] (4)

A solution of 3,5(S)-O-benzylidene-1,4-dideoxy-1,4-imino-L-arabinitol (13) (400 mg, 1.81 mmol) in aqueous sulfuric acid (0.1N, 20 ml) was heated at 100° C. for 3 hours. The cooled reaction mixture was neutralized by the slow addition of 50% aqueous sodium hydroxide. The resulting mixture was concentrated by rotary evaporation, removing residual water by azeotroping with toluene. The residue was purified by flash chromatography using 2/98 NH$_4$OH/ethanol as the eluent. The appropriate fractions were combined and concentrated by rotary evaporation to provide the free amine (0.24 g; 90%) as a yellow oil. This oil was dissolved in methanol (6 ml) and aqueous hydrochloric acid (12M, 0.15 ml) was slowly added. After 10 min. ether (5 ml) was slowly added. After cooling to 5° C. the solid was collected by filtration and dried in a vacuum oven to yield 1,4-dideoxy-1,4-imino-L-arabinitol hydrochloride [LAB1] (4), (0.258 g, 84%) as a white (KBr): 3410, 33601 30101 solid, m.p. 165.5°-166° C.; $v_{max}$ (KBr): 3410, 3360, 3010, 2960, 2740. 1570; 1390, 1370; 1255, 1070; 1000, 960; $^1$H NMR (CD$_3$OD) ∂ 3.30 (t, 1 H), 3.50 (m, 2 H), 3.80 (m, 2 H), 3.95 (s 1 H), 4.20 (t, 1 H); $^{13}$C NMR (CD$_3$OD) ∂ 51.71, 60.61; 60.66, 69.43, 75.96, 77.27; $[\alpha]_{D25}$−32.9° (c 0.319, H$_2$O).

REFERENCES

1. Winchester and Fleet *Glycobiology*, 2, 199 (1992).
2. Fairbanks et al., *Tetrahedron*, 48, 3365-3376 (1992).
3. Fellows et al., *Nitrogen Metabolism of Plants*, (Ed. K. Mengl and D. J. Pilbeam), Clarendon Press, Oxford, pp. 271-284 (1992).
4. Nash et al., The Identification of a Hydroxylated Pyrrolidine Derivative from *J. Chem. Soc., Chem. Commun.*, 738 (1985).
5. Kayakiri et al., *Tetrahedron Lett.*, 29, 1725 (1988).
6. Kayakiri et al., *Chem. Pharm. Bull.* 39, 2807 (1991).
7. Nash et al., *Phytochemistry* 24, 1620 (1985).
8. Furukawa et al., *Phytochemistry* 24, 593 (1985).
9. Fleet et al., *Tetrahedron Lett.*, 26, 3127 (1985).
10. Scofield et al., *Life Sci.* 645, 39 (1986).
11. Simmonds et al., *J, Chem. Ecol.* 16, 3167 (1990).
12. Rosenkranz and Klopman, *Carcinogenesis* (London) 11, 349 (1990).
13. Scofield et al., *Phytochemistry* 107 (1990).
14. Akoki and Hatanaka, *Phytochemistry* 30, 3197 (1991).
15. Wyn et al., *Tetrahedron Lett.* 26, 3125 (1985).
16. Fleet and Smith, *Tetrahedron* 42, 5685 (1986).
17. Fleet and Witty, *Tetrahedron: Asymmetry* 1, 119 (1990); Fleet et al. *Tetrahedron* 44, 2649 (1988); Witte and McClard, *Tetrahedron Lett.* 32, 3927 (1991); Fleet and Son, *Tetrahedron* 44, 2637 (1988) ; Wehner and Jaeger, *Angew, Chem.* 102 1180 (1990) ; Dureault et al., *J. Carbohydr, Chem.* 9, 121 (1990) ; Iiosaka et al., *Bull. Chem. Soc. Jpn.* 62, 797 (1989) ; Naleway et al., *Carbohydr, Res.* 179, 199 (1988) ; Austin et al., *Tetrahedron* 43, 3095 (1987) ; Bashyal et al., *Tetrahedron* 43, 3083 (1987); Setoi et al., *Chem. Pharm. Bull.* 35, 3995 (1987).
18. Ikota and Hanaki, *Chem. Pharm. Bull.* 35, 2140 (1987).
19. Ziegler et al., *Angew. Chem.* 100, 737 (1988); Pederson and Wong, *Heterocycles* 28, 477 (1989); Von der Osten et al., *J. Am. Chem. Soc,* 111, 3924 (1989); Hung et al., *J. Org. Chem.* 56, 3849 (1991); Kajimoto et al., *J. Am. Chem. Soc,* 113, 9009 (1991).
20. Hassan, *Gazz. Chim. Ital.* 122, 7 (1992).
21. Axamawaty et al., *Biochem, J.* 266, 245 (1990).
22. Scofield et al., *Life Sci.* 39, 645 (1986).
23. Robinson et al., *Drugs of the Future* 17, 705, (1992).
24. Fleet et al., *FEBS Lett.* 237, 128 (1988).
25. Karpas et al., *Proc. Nat. Acad. Sci. US* 85, 9229 (1988).
26. Koszyk et al., *Chem. Abs.* 112, 179794 (1990); U.S. Pat. No. 4,876,268, 24 Oct. 1989.
27. Humphlett et al., *Carbohydr. Res.* 4, 157 (1967).
28. Fleet et al., *J. Chem. Soc. Perkin Trans.* 1, 665 (1989).
29. Wang et al., *Tetrahedron: Asymm.* 1, 527 (1990).
30. Baldwin, *J. Chem. Soc., Chem. Commun.*, 734 (1976).

Various other examples will be apparent to the person skilled in the art after reading the present disclosure without departing from the spirit and scope of the invention. It is intended that all such other examples be included within the scope of the appended claims.

What is claimed is:

1. A method for the chemical synthesis of 1,4-dideoxy-1,4-imino-L-arabinitol from D-lyxonolactone comprising:
   a) introducing a protecting group at C-3 and C-5 by reacting D-lyxonolactone with benzaldehyde to give the corresponding benzylidine derivative,
   b) esterifying the benzylidine derivative at C-2 with mesyl chloride to give the corresponding mesylate,
   c) reducing the mesylate with lithium borohydride to open up the ring and give the corresponding D-lyxitol,
   d) reacting the D-lyxitol with potassium carbonate in alcoholic solution to give the corresponding C-1/C-2 epoxide,
   e) esterifying the epoxide with triflic anhydride to give the corresponding triflate ester,
   f) introducing the azide group at C-4 in the triflate ester to give the corresponding azidoepoxide,
   g) reducing the azide group of azidoepoxide by catalytic hydrogenation to provide the corresponding amine,
   h) reacting the amine with tetrabutylammonium iodide to provide ring closure to the desired pyrrolidine structure and give the protected 1,4-dideoxy-1,4-imino-L-arabinitol,
   i) removing the benzylidine protecting group of the protected 1,4-dideoxy-1,4-imino-L-arabinitol by acid hydrolysis to give the desired 1,4-dideoxy-1,4-imino-L-arabinitol.

2. The method of claim 1 in which the azide group is introduced by reaction of the triflate ester with sodium azide.

3. The method of claim 1 in which the catalytic hydrogenation is carried out by reaction in the, presence of palladium catalyst.

4. The method of claim 1 in which the 1,4-dideoxy-1,4-imino-L-arabinitol is isolated as the hydrochloride salt.

5. The method of claim 1 in which the azide group is introduced by reaction of the triflate ester with sodium azide, the catalytic hydrogenation is carried out by reaction in the presence of palladium catalyst and the 1,4-dideoxy-1,4-imino-L-arabinitol is isolated as the hydrochloride salt.

* * * * *